(12) United States Patent
Chiu et al.

(10) Patent No.: US 11,974,875 B2
(45) Date of Patent: May 7, 2024

(54) METHODS FOR PRODUCING SILVER-AMENDED CARBON MATERIALS

(71) Applicants: Pei-Chun Chiu, Middletown, DE (US); Danhui Xin, Newark, DE (US); Steven Lobo, II, Raleigh, NC (US)

(72) Inventors: Pei-Chun Chiu, Middletown, DE (US); Danhui Xin, Newark, DE (US); Steven Lobo, II, Raleigh, NC (US)

(73) Assignee: University of Delaware, Newark, DE (US)

(*) Notice: Subject to any disclaimer, the term of this patent is extended or adjusted under 35 U.S.C. 154(b) by 645 days.

(21) Appl. No.: 17/258,798

(22) PCT Filed: Jul. 12, 2019

(86) PCT No.: PCT/US2019/041530
§ 371 (c)(1),
(2) Date: Jan. 8, 2021

(87) PCT Pub. No.: WO2020/014565
PCT Pub. Date: Jan. 16, 2020

(65) Prior Publication Data
US 2021/0269311 A1  Sep. 2, 2021

Related U.S. Application Data

(60) Provisional application No. 62/697,428, filed on Jul. 13, 2018.

(51) Int. Cl.
*C01B 32/05* (2017.01)
*A61B 6/00* (2006.01)
(Continued)

(52) U.S. Cl.
CPC ............ *A61B 6/583* (2013.01); *A61B 6/482* (2013.01); *A61B 6/505* (2013.01); *B01J 20/20* (2013.01);
(Continued)

(58) Field of Classification Search
CPC ..................................................... C01B 32/05
See application file for complete search history.

(56) References Cited

U.S. PATENT DOCUMENTS 3,294,572 A    12/1966  Piccione et al.
2009/0068241 A1  3/2009  Britz et al.
(Continued)

OTHER PUBLICATIONS

Acevedo et al., "Efficiency Study of Silver Nanoparticles (AgNPs) Supported on Granular Activated Carbon against *Escherichia coli*", J. Nanomedicine Research 1(2):00009, 2014, 5 pages.
(Continued)

*Primary Examiner* — Brian A McCaig
(74) *Attorney, Agent, or Firm* — BUCHANAN, INGERSOLL & ROONEY PC (57) ABSTRACT

Silver-amended carbon materials containing silver nanoparticles are prepared by a process involving an initial reduction of a porous carbon material, followed by contacting the reduced porous carbon material with an aqueous solution of a silver salt. Such silver-amended carbon materials may contain a relatively high loading of silver nanoparticles on both the outside surface and within the interior of the porous carbon material and are useful for disinfecting and/or otherwise purifying fluids such as microbe-containing fluids.

22 Claims, 7 Drawing Sheets

(51) Int. Cl.
  A61B 6/50 (2024.01)
  A61B 6/58 (2024.01)
  B01J 20/20 (2006.01)
(52) U.S. Cl.
  CPC ....... *C01B 32/05* (2017.08); *B01J 2220/4806* (2013.01); *C01P 2002/74* (2013.01); *C01P 2006/12* (2013.01)

(56) References Cited

U.S. PATENT DOCUMENTS

| | | | |
|---|---|---|---|
| 2013/0240439 | A1 | 9/2013 | Pradeep et al. |
| 2015/0224484 | A1* | 8/2015 | Kim .................. B01J 35/0013 564/305 |
| 2017/0313604 | A1* | 11/2017 | Garibi ...................... C02F 1/50 |
| 2017/0354948 | A1 | 12/2017 | Saleh et al. |

OTHER PUBLICATIONS

Alimohammadi et al., "Deposition of silver nanoparticles on carbon nanotube by chemical reduction method: Evaluation of surface, thermal and optical properties", Superlattices and Microstructures 52 (2012) 50-62.

Chiang et al., "Synthesis of Silver Particle onto Bamboo Charcoal by Tripropylene Glycol and the Composites Characterization", Materials 2014, 7, 742-750, 9 pages.

El-Aassar et al., "Using Silver Nanoparticles Coated on Activated Carbon Granules in Columns for Microbiological Pollutants Water Disinfection in Abu Rawash area, Great Cairo, Egypt," Australian Journal of Basic and Applied Sciences, 7(1): 422-432, 2013.

Eltugral et al., "Preparation of nano-silver-supported activated carbon using different ligands," Res Chem Intermed DOI 10.1007/s11164-015-2110-6, published online May 29, 2015, 15 pages.

Huang et al., "Facile pyrolysis preparation of rosin-derived biochar for supporting silver nanoparticles with antibacterial activity". Composites Science and Technology 145 (2017), 89-95.

Klüpfel et al., "Redox Properties of Plant Biomass-Derived Black Carbon (Biochar)", Environ. Sci. Technol. 48, 2014, 5601-5611.

Ma et al., "Carbon Foam Decorated with Silver Nanoparticles for Electrochemical $CO_2$ Conversion", Energy Technol. 2017, 5, 861-863.

Prevoteau et al. "The electron donating capacity of biochar is dramatically underestimated", Scientific Reports. 6:32870, 11 pages.

Saha et al. "Effect of Pyrolysis Temperature on Acidic Oxygen-Containing Functional Groups and Electron Storage Capacities of Pyrolyzed Hydrochars", ACS Sustainable Chem. Eng., 2019, 7, pp. 8387-8396.

Saquing et al., "Wood-Derived Black Carbon (Biochar) as a Microbial Electron Donor and Acceptor", Environ Sci. Tech Let, 2016, 3, (2), 62-66, 10 pages.

Wu et al., "Modified biochar supported Ag/Fe nanoparticles used for removal of cephalexin in solution: Characterization, kinetics and mechanisms", Colloids and Surfaces, A Physicochem. Eng. Aspects 517, 2017, 10 pages.

Xin et al., "Chemical methods for determining the electron storage capacity of black carbon", MethodsX 5 (2018), pp. 1515-1520.

Xin et al., "New methods for assessing electron storage capacity and redox reversibility of biochar". Chemosphere 215 (2019), pp. 827-834.

Yi et al., "The Origin and Reversible Nature of Poultry Litter Biochar Hydrophobicity", J. Environ. Qual. 44:963-971 (2015).

International Preliminary Report on Patentability for Application No. PCT/US2019/041530, dated Jan. 19, 2021, 6 pages.

International Search Report and Written Opinion for International Application PCT/US2019/041530, dated Oct. 18, 2019, 7 pages.

Klüpfel et al., "Redox Properties of Plant Biomass-Derived Black Carbon (Biochar)", Supporting Information, Mar. 26, 2021, 22 pages.

Prevoteau et al. "The electron donating capacity of biochar is dramatically underestimated", Supplementary Information, Mar. 26, 2021, 21 pages.

* cited by examiner

METHODS FOR PRODUCING SILVER-AMENDED CARBON MATERIALS

CROSS-REFERENCE TO RELATED APPLICATIONS

This application is a national stage application under 35 U.S.C. § 371 of International Application No. PCT/US2019/041530, filed Jul. 12, 2019, which claims priority to United States Provisional Application No. 62/697,428 filed Jul. 13, 2018, the disclosures of each of these applications being incorporated herein by reference in their entireties for all purposes.

GOVERNMENT LICENSE RIGHTS

This invention was made with government support under Contract No. 20166800725064 awarded by the United States Department of Agriculture—National Institute of Food and Agriculture (USDA-NIFA). The government has certain rights in the invention.

FIELD OF THE INVENTION

The present invention pertains to silver-amended carbon materials useful for the purification and treatment of fluids such as drinking water and irrigation water, as well as methods for preparing such silver-amended carbon materials.

BACKGROUND OF THE RELATED ART

The use of silver as a disinfectant against various types of microbes has been known for some time, with metallic silver nanoparticles being of particular interest in such applications. Because silver nanoparticles by themselves are difficult to handle and are prone to aggregation, there has been considerable effort devoted to supporting such nanoparticles on carrier matrices such as activated carbon and the like. Typically, such supported silver products are prepared by treating an aqueous mixture of a carrier matrix and a soluble silver salt with a reducing agent, whereby the silver salt is reduced to Ag(0). The following publications describe such an approach:

Acevedo et al. (2014) Efficiency Study of Silver Nanoparticles (AgNPs) Supported on Granular Activated Carbon against *Escherichia coli*. J. Nanomed Res 1(2): 00009.

El-Aassar et al., Using Silver Nanoparticles Coated on Activated Carbon Granules in Columns for Microbiological Pollutants Water Disinfection in Abu Rawash area, Great Cairo, Egypt, Australian Journal of Basic and Applied Sciences, 7(1): 422-432, 2013.

Wu et al., Modified biochar supported Ag/Fe nanoparticles used for removal of cephalexin in solution: Characterization, kinetics and mechanisms, Colloids and Surfaces A: Physicochem. Eng. Aspects 517 (2017 63-71.

Eltugral et al., Preparation of nano-silver-supported activated carbon using different ligands, Res Chem Intermed DOI 10.1007/s11164-015-2110-6, published online 29 May 2015.

Chiang et al., Synthesis of Silver Particle onto Bamboo Charcoal by Tripropylene Glycol and the Composites Characterization, Materials 2014, 7, 742-750.

Huang et al., Facile pyrolysis preparation of rosin-derived biochar for supporting silver nanoparticles with antibacterial activity, Composites Science and Technology 145 (2017) 89-95.

Alimohammadi et al., Deposition of silver nanoparticles on carbon nanotube by chemical reduction method: Evaluation of surface, thermal and optical properties, Superlattices and Microstructures 52 (2012) 50-62.

Xin et al., Decoration of carbon nanotubes with silver nanoparticles for advanced CNT/polymer nanocomposites, Composites: Part A 42 (2011) 961-967.

Ma et al., Carbon Foam Decorated with Silver Nanoparticles for Electrochemical $CO_2$ Conversion, Energy Technol. 2017, 5, 861-863.

Despite the work done to date in this field, there remains a need for alternative, improved methods for preparing silver nanoparticle-containing carbon materials which provide better control over the location and size of the silver nanoparticles and permit the incorporation of relatively high loadings of silver.

SUMMARY OF THE INVENTION

According to certain embodiments, the present invention provides a method of incorporating a substantial, predictable, tunable (adjustable) and regenerable amount of silver, primarily in the form of silver (Ag(0)) nanoparticles, into a porous solid carbon, such as activated carbon or biochar. The resulting silver-amended carbon material can serve as a long-lasting, antimicrobial filter medium for the purification and disinfection of, e.g., drinking water, irrigation water, humidified air, and other fluids wherein the presence of bacteria, viruses and other microbes (i.e., microorganisms, including microbial pathogens) is of concern.

Various non-limiting aspects of the present invention may be summarized as follows:

Aspect 1: A method of preparing a silver-amended carbon material, comprising a step of:
  contacting a reduced porous carbon material with an aqueous solution of a silver salt, whereby the reduced porous carbon material acts as a reducing agent with respect to the silver salt and reduces the silver salt to form Ag(0) which deposits in the form of nanoparticles within and on the exterior of the reduced porous carbon material.

Aspect 2: The method of Aspect 1, wherein the reduced porous carbon material is prepared by contacting a starting porous carbon material having an electron storage capacity with a pre-determined amount of a reducing agent in an aqueous solution to obtain the reduced porous carbon material, wherein the reducing agent is capable of donating electrons to the starting porous carbon material.

Aspect 3: The method of Aspect 2, wherein the electron storage capacity of the starting porous carbon material is at least 0.5 mmol/g.

Aspect 4: The method of Aspect 2 or 3, wherein the starting porous carbon material is selected from the group consisting of biochars, activated carbons, hydrochars, pyrolyzed hydrochars, soot, graphite, graphene oxides, fullerenes, char, charcoal, and carbon nanotubes.

Aspect 5: The method of any of Aspects 1 to 4, wherein the contacting of the reduced porous carbon material with the aqueous solution of the silver salt is carried out at a pH of from 3 to 8, 4 to 8, or 5 to 8.

Aspect 6: The method of any of Aspects 2 to 4, wherein the reducing agent is selected from the group consisting of dithionites, thiosulfates, (poly)sulfides, cysteine, glutathione, titanium (III) compounds and complexes, iron (II) compounds and complexes, borohydrides, aluminum hydrides, hydrazine, and hydroxylamine.

Aspect 7: The method of any of Aspects 1 to 6, wherein the silver salt is selected from the group consisting of silver nitrate, silver sulfate, silver perchlorate, silver acetate, silver nitrite, silver bicarbonate and combinations thereof.

Aspect 8: The method of any of Aspects 2 to 4 or 6, wherein the contacting of the starting porous carbon material with the pre-determined amount of a reducing agent is carried out under oxygen-free or oxygen-limited conditions.

Aspect 9: The method of any of Aspects 2 to 4, 6 or 8, wherein the predetermined amount of reducing agent used is an amount which is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the electron storage capacity of the starting porous carbon material.

Aspect 10: The method of any of Aspects 2 to 4, 6 or 8, wherein the predetermined amount of reducing agent used is an amount which is in excess of the electron storage capacity of the starting porous carbon material.

Aspect 11: The method of any of Aspects 2 to 4, 6 or 8 to 10, wherein the reduced porous carbon material is fully reduced, as measured by the electron storage capacity.

Aspect 12: The method of any of Aspects 2 to 4, 6 or 8 to 11, wherein an amount of silver salt is used which is selected based on the electron storage capacity of the starting porous carbon material.

Aspect 13: The method of any of Aspects 2 to 4, 6 or 8 to 12, wherein the reduced porous carbon material has been collected, rinsed with water, and optionally dried prior to being contacted with the aqueous solution of the silver salt.

Aspect 14: The method of any of Aspects 1 to 13, wherein the aqueous solution of the silver salt is added incrementally to an aqueous suspension of the reduced porous carbon material.

Aspect 15: The method of Aspect 14, wherein the aqueous solution of the silver salt is added at a rate effective to maintain an $Ag^+$ concentration in the aqueous suspension of at least 0.1 mM.

Aspect 16: The method of any of Aspects 1 to 15, wherein the silver-amended carbon material is comprised of at least 5%, at least 10%, at least 15%, at least 20%, at least 25%, at least 30%, or at least 35% by weight silver based on the total weight of the silver-amended carbon material.

Aspect 17: The method of any of Aspects 1 to 16, wherein the silver nanoparticles have an average size of 1 to 100 nm as determined by XRD analysis.

Aspect 18: The method of any of Aspects 1 to 17, wherein at least 50%, at least 55%, at least 60%, at least 65%, at least 70%, at least 75%, at least 80%, at least 85%, or at least 90% of the silver in the silver-amended carbon material is in the form of elemental silver.

Aspect 19: The method of any of Aspects 1 to 18, wherein the silver-amended carbon material is in a form selected from the group consisting of powder, granules, fibers, blocks and nanotubes.

Aspect 20: The method of any of Aspects 2 to 4, 6 or 8 to 11, wherein the starting porous carbon material has a BET surface area of at least 10 $m^2/g$.

Aspect 21: The method of any of Aspects 2 to 4, 8 to 12 or 20, wherein the starting porous carbon material has an internal porosity of at least 5%, at least 10%, at least 15%, at least 20%, at least 25%, at least 30%, at least 35%, at least 40%, at least 45%, at least 50%, at least 55% or at least 60%.

Aspect 22: A silver-amended carbon material produced by the method of any of Aspects 1 to 21.

Aspect 23: A method of purifying and disinfecting a fluid containing microbes comprising contacting the fluid with a silver-amended carbon material produced by the method of any of Aspects 1 to 21.

Aspect 24: The method of Aspect 23, wherein the fluid additionally comprises one or more contaminants selected from the group consisting of organic pollutants and metal ions.

DETAILED DESCRIPTION OF THE INVENTION

In accordance with the present invention, a silver-amended carbon material may be prepared by contacting a reduced porous carbon material with an aqueous solution of a silver salt, whereby the reduced porous carbon material acts as a reducing agent with respect to the silver salt and reduces the silver salt to form Ag(0) which deposits in the form of nanoparticles within and on the exterior of the reduced porous carbon material to produce the silver-amended carbon material. The silver nanoparticles can be in direct contact with internal and external surfaces of the reduced porous carbon material. The reduced porous carbon material may be prepared by contacting a starting porous carbon material having an electron storage capacity with a pre-determined amount of a reducing agent in an aqueous solution to obtain the reduced porous carbon material, wherein the reducing agent is capable of donating electrons to the starting porous carbon material. The reduced porous carbon material may be directly or immediately contacted with the aqueous solution of the silver salt to obtain the silver-amended carbon material. However, this is not required. Thus, in certain embodiments of the invention, the reduced porous carbon material is prepared and then stored or held for a certain period of time before being subjected to the treatment with the aqueous solution of silver salt. The reduced porous carbon material may be stored or held under an inert atmosphere to prevent or minimize any unwanted re-oxidation. For example, the reduced porous carbon material may be produced at one location and then transported to a different location to be converted into the silver-amended carbon material. Thus, the two steps (reduction of the starting porous carbon material, contact with silver salt in aqueous solution) are performed sequentially, but may be separated in time and/or location.

The porous carbon material used as a starting material in the present invention may be derived from any suitable source using known methods. As used herein, the term "porous carbon material" refers to a material which is porous and comprised predominantly, but not necessarily exclusively, of carbon in its elemental form. For example, the porous carbon material may, and preferably does, contain some amount of functionality, such as functional groups comprised of non-carbon elements such as oxygen, nitrogen and/or hydrogen (for example, quinone, carboxyl, carbonyl, hydroxyl and/or phenolic functional groups), as well as residual ash and the like. Suitable types of porous carbon materials include, for example, biochars, activated carbons, hydrochars, pyrolyzed hydrochars, soot, graphite, graphene oxides, fullerenes, char, charcoal, and carbon nanotubes. Any of the materials referred to in the art as "black carbon" or "carbon black" may be employed. The porous carbon material may or may not be activated using any of the activation techniques known in the art. The porous carbon material may be in any suitable or desired physical form such as powder, granules, fibers, blocks, nanotubes and the like and combinations thereof. Typically, it will be preferred for the porous carbon material to have a relatively high degree of internal porosity. For instance, the internal porosity of the starting porous carbon material may be at least 5%, at least 10%, at least 15%, at least 20%, at least 25%, at least 30%, at least 35%, at least 40%, at least 45%, at least 50%, at least 55% or at least 60%. Internal porosity can be measured by the gravimetric method, by mercury intrusion porosimetry, or by computed tomographic (CT) analysis. For example, ASTM D4284-12 (2017) describes a method which uses mercury intrusion porosimetry to measure internal porosity. Generally speaking, the starting porous carbon material preferably has a relatively high BET surface area, e.g., a BET surface area of at least 10 $m^2/g$, at least 25 $m^2/g$, at least 50 $m^2/g$, at least 100 $m^2/g$, at least 200 $m^2/g$, at least 300 $m^2/g$, at least 400 $m^2/g$, at least 500 $m^2/g$, at least 600 $m^2/g$, at least 700 $m^2/g$, or at least 800 $m^2/g$. BET surface area can be measured using ASTM test method D6556-19.

According to certain embodiments of the invention, the starting porous carbon material is selected to have a comparatively high electron storage capacity. The electron storage capacity of the starting porous carbon material will influence the amount of elemental silver (Ag(0)) which can be loaded into the porous carbon material using the process of the present invention. That is, the higher the electron storage capacity, the greater the amount of silver nanoparticles that potentially can be introduced. Thus, the electron storage capacity of the starting porous carbon material (on a dry weight basis) can be at least 0.5 mmol/g, at least 1 mmol/g, at least 1.5 mmol/g, at least 2 mmol/g, at least 2.5 mmol/g, at least 3 mmol/g, at least 3.5 mmol/g, at least 4 mmol/g, at least 4.5 mmol/g, at least 5 mmol/g, at least 5.5 mmol/g, at least 6 mmol/g, or at least 6.5 mmol/g, in various embodiments of the invention.

Figure 7:
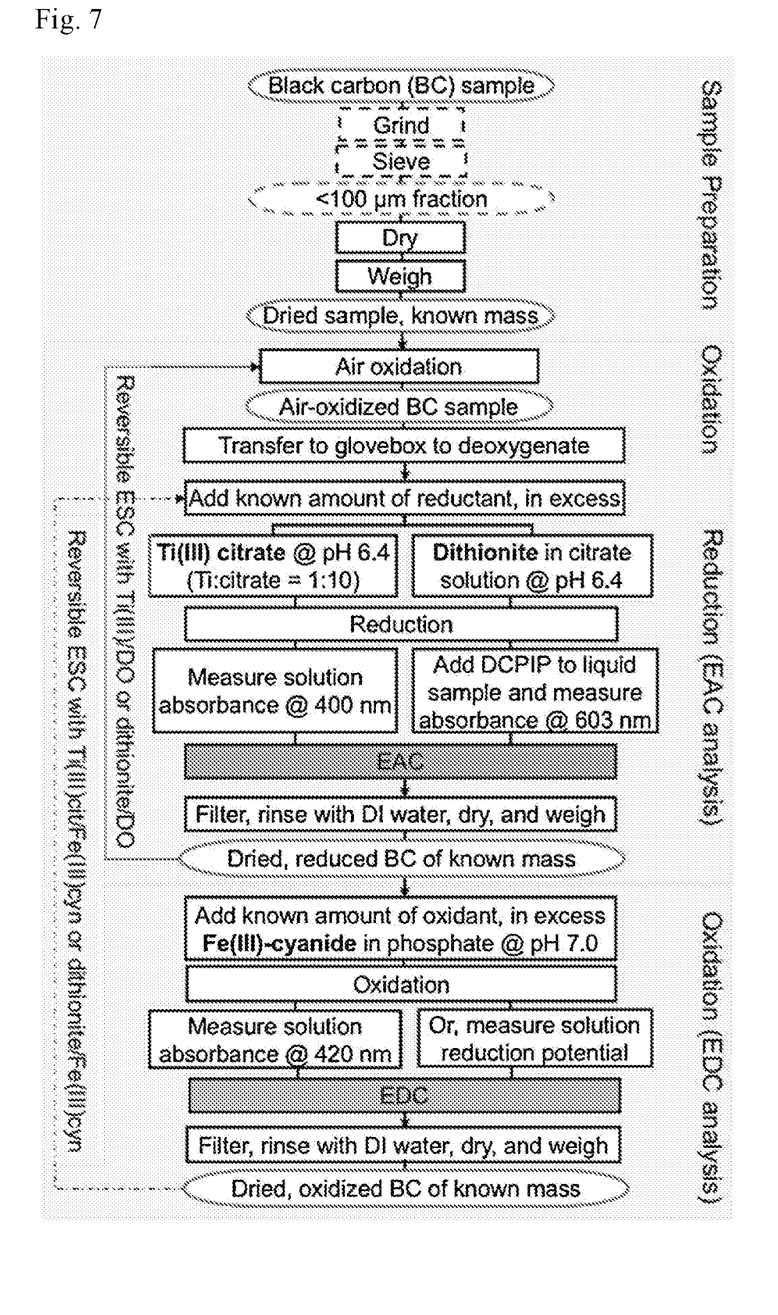
FIG. 7 depicts, in summary form, how the electron storage capacity of a porous carbon material is experimentally measured.

The electron storage capacity (ESC) of the starting porous carbon material can be measured by the method described in Xin et al., Chemical methods for determining the electron storage capacity of black carbon, MethodsX 5 (2018) 1515-1520, the entire disclosure of which is incorporated herein by reference for all purposes. In such method, a pair of a reductant (Ti(III) citrate or dithionite) and an oxidant (ferricyanide or dissolved oxygen) of appropriate redox potentials is used to reduce and oxidize, respectively, the porous carbon material. This can be done repeatedly for multiple cycles. The amount of electrons added (by the reductant) to, and/or removed (by the oxidant) from, the porous carbon material, which can be determined spectrometrically or electrochemically from changes in reductant or oxidant concentration in solution, is the electron storage capacity of the porous carbon material. The experimental steps involved in measuring electron storage capacity are summarized in FIG. 1 of the article (reproduced herein as FIG. 7).

The function of the reducing agent is to reduce the starting porous carbon material, prior to introduction of silver ions. Thus, a suitable reducing agent may be any substance, organic or inorganic, that is capable of transferring electrons to the starting porous carbon material. According to certain embodiments, the reducing agent has a redox potential of less than 0.8 V (vs. standard hydrogen electrode). Preferably, the reducing agent is water soluble (e.g., has a solubility in water at 25° C. of at least 1 g/L). Combinations of different reducing agents may be employed. Suitable types of reducing agents include, for example, dithionites (such as sodium dithionite), thiosulfates, (poly)sulfides, cysteine, glutathione, titanium (III) compounds and complexes (such as titanium citrate), iron (II) compounds and complexes, borohydrides (such as sodium borohydride), aluminum hydrides, hydrazine, hydroxylamine, and the like and combinations thereof.

The amount of reducing agent employed, relative to the amount of starting porous carbon material, is selected based on the electron storage capacity of the material and the degree of reduction which is desired. The degree to which the starting porous carbon material is reduced will influence the loading of silver which can be achieved in the silver-amended carbon material obtained as the product of the inventive method. The more reduced the starting porous carbon material is, the greater the quantity of electrons that will be present in the material and available to interact with the silver salt to generate Ag(0). For example, the amount of reducing agent used may be a predetermined amount which is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the electron storage capacity of the starting porous carbon material. According to one embodiment, the predetermined amount of reducing agent used is an amount which is in excess of the electron storage capacity of the starting porous carbon material. Such an amount will help ensure that the porous carbon material is fully reduced and thus capable of maximizing the silver loading achievable in the silver-amended carbon material.

In preferred embodiments of the invention, the reducing agent is contacted with the starting porous carbon material in the form of an aqueous solution. Typically, water is the only liquid carrier (solvent) present in the aqueous solution, although water miscible organic solvents could be used in combination with the water. The concentration of reducing agent in the aqueous solution is not regarded as critical; reducing agent concentrations of from 1 to 100 mM can be employed, for example. In addition to the reducing agent(s), one or more substances such as buffers could also be present in the aqueous solution. The pH of the aqueous solution may be, for example, from 3 to 8, 4 to 8, or 5 to 8. The aqueous solution containing the reducing agent may be contacted with the starting porous carbon material for a time and at a temperature effective to achieve the desired degree of reduction in the material. The aqueous solution and starting porous carbon material may be combined all at once or incrementally (e.g., the aqueous solution may be added in portions or aliquots). The mixture of aqueous solution and starting porous carbon material may be stirred or otherwise agitated. The contacting of the aqueous solution and starting porous carbon material may, for instance, be conveniently be carried out at around ambient or room temperature, e.g., 10° C. to 40° C., but higher temperatures could also be utilized. The contacting step may preferably be carried out under oxygen-free or oxygen-limited conditions, such as under an oxygen-free atmosphere. In the context of the present invention, "oxygen-limited conditions" means conditions in which the molecular oxygen concentration is reduced as compared to conditions corresponding to normal atmospheric conditions in which no steps are taken to reduce the amount of molecular oxygen present. The contacting time according to certain non-limiting aspects of the invention may be from 0.5 hours to 5 days.

Once the desired degree of reduction of the porous carbon material has been achieved, the resulting reduced porous carbon material may be separated from the remaining aqueous solution and subjected to one or more further processing steps before being contacted with an aqueous solution comprised of silver salt. For example, the reduced porous carbon material may be collected by filtration, centrifugation or other such separation method, rinsed (for example, with pure water, e.g., deoxygenated/deionized water, to remove water soluble species still present), and then dried. However, such further processing is not required.

As previously mentioned, the reduced porous carbon material is contacted with an aqueous solution of a silver salt, whereby the reduced porous carbon material acts as a reducing agent with respect to the silver salt and reduces the silver salt to form Ag(0) which deposits in the form of nanoparticles within and on the exterior of the reduced porous carbon material to produce the silver-amended carbon material.

Preferably, the silver salt is a salt which is water soluble; for example, a silver salt may be employed which has a solubility in water at 25° C. of at least 1 g/L, preferably at least 10 g/L. When dissolved in water, the silver salt preferably dissociates to form $Ag^+$ ions. Suitable silver salts include, for example, silver nitrate, silver sulfate, silver perchlorate, silver acetate, silver nitrite, silver bicarbonate and combinations thereof. The use of silver nitrate is particularly preferred.

Typically, water is the only liquid carrier (solvent) present in the aqueous solution containing the silver salt, although water miscible organic solvents could be used in combination with the water. The concentration of silver salt in the aqueous solution is not regarded as critical; silver salt concentrations of from 5 to 200 mM can be employed, for example. According to one embodiment, the reduced porous carbon material is first combined with water that does not contain silver nitrate to form an initial mixture (which may be in the form of a suspension, for example). An aqueous solution comprised of silver salt may then be combined with the initial mixture, either all at once or incrementally. In addition to the silver salt(s), one or more substances such as other types of salts (e.g., sodium nitrate) could also be present in the aqueous solution. The pH of the aqueous solution may be, for example, from 3 to 8, 4 to 8, or 5 to 8. Preferably, the pH of the aqueous phase during the contacting of the silver salt-containing aqueous solution with the reduced porous carbon material is maintained between 5 and 8. It has been found that by operating within this pH range, problems with precipitation of $Ag^+$ species may be avoided or reduced. Additionally, the pH value during the contacting step has an influence on the amount of silver loading achieved in the resulting silver-amended carbon material. The pH may be monitored and adjusted by addition of acid or base to maintain the pH within this preferred range or at a desired value during the contacting of the silver salt salt aqueous solution with the reduced porous carbon material. Thus, in certain embodiments, the contacting of the silver salt-containing aqueous solution with the reduced porous carbon material is carried out at a controlled pH.

The aqueous solution containing the silver salt may be contacted with the reduced porous carbon material for a time and at a temperature effective to achieve the desired amount of Ag(0) incorporation in the material. The silver salt-containing aqueous solution and reduced porous carbon material may be combined all at once or incrementally (e.g., the aqueous solution may be added in portions or aliquots). According to certain aspects of the invention, the $Ag^+$ content of the liquid phase is monitored and additional amounts of silver salt are added as necessary to maintain the $Ag^+$ content at 0.1 mM or higher, 0.5 mM or higher, or 1 mM or higher. The mixture of silver salt-containing aqueous solution and reduced porous carbon material may be stirred, shaken or otherwise agitated. The contacting of the aqueous solution of silver salt and reduced porous carbon material may, for instance, be conveniently be carried out at around ambient or room temperature, e.g., 10° C. to 40° C., but higher temperatures could also be utilized. The contacting time according to certain non-limiting aspects of the invention may be from 0.5 hours to 5 days.

Once the desired degree of silver incorporation into the porous carbon material has been achieved, the resulting silver-amended carbon material may be separated from the remaining aqueous solution and subjected to one or more further processing steps. For example, the silver-amended carbon material may be collected by filtration, centrifugation or other such separation method, rinsed (for example, with pure water, e.g., deoxygenated/deionized water, to remove water soluble species still present), and then dried.

The preparation method of the present invention enables the production of silver-amended carbon materials having tunable properties and attributes. For example, the silver loading can be readily adjusted by controlling parameters such as the electron storage capacity of the starting porous carbon material, the quantity of electrons stored in the reduced porous carbon material as a result of the reductive effect of the reducing agent, the quantity of silver salt contacted with the reduced porous carbon material, and the pH of the aqueous phase during such contacting.

According to various aspects of the invention, the silver-amended carbon material may be comprised of at least 5%, at least 10%, at least 15%, at least 20%, at least 25%, at least 30%, or at least 35% by weight silver based on the total weight of the silver-amended carbon material. At least 50%, at least 55%, at least 60%, at least 65%, at least 70%, at least 75%, at least 80%, at least 85%, or at least 90% (on a molar basis) of the silver in the silver-amended carbon material may be in the form of elemental silver. The balance of the silver may be in ionic form ($Ag^+$). The silver nanoparticles present in the silver-amended carbon material may have an average size of 1 to 100 nm or 10 to 50 nm as determined by XRD analysis. In certain embodiments of the invention, the silver nanoparticles may have a size distribution such that at least 90%, at least 95%, at least 99% or even 100% of the silver nanoparticles have a particle size within the range of from 1 to 100 nm.

As a consequence of the particular way in which they are prepared, in accordance with the present invention, the silver nanoparticles are present both within and on the exterior of the porous carbon material. Moreover, the silver nanoparticles can be in direct contact with internal and external surfaces of the porous carbon material. Thus, there is advantageously not any other substance such as iron which is disposed between the silver nanoparticles and the surface of the porous carbon material component of the silver-amended carbon material. Thus, in certain embodiments, no iron is disposed between the silver nanoparticles and the porous carbon material surface. In other embodiments, the silver-amended carbon material is free of iron (less than 100 ppm Fe). Additionally, the synthetic method employed in the present invention permits substantial amounts of silver nanoparticles to be deposited within the pores, rather than predominantly or entirely on the exterior (outside) surface of the carbon material, in contrast to methods known in the prior art where a carbon material is treated with a reducing agent after being combined with a silver salt solution. According to certain embodiments, at least a fraction of the silver nanoparticles may be present in the form of very small nanoparticles (e.g., 1 to 5 nm) which are present within the pores of the carbon material.

The silver-amended carbon materials of the present invention may be in a form selected from the group consisting of powder, granules, fibers, blocks and nanotubes and are useful in a wide variety of end uses such as the purification and/or disinfection of various types of fluids (including both liquid and gaseous fluids). For example, the present invention provides a method of purifying and disinfecting a fluid containing microbes (such as, but not limited to, microbial pathogens) which comprises contacting the fluid with a silver-amended carbon material produced by the above-described processes. The fluid may additionally comprise one or more contaminants selected from the group consisting of organic pollutants (such as hydrophobic organic compounds) and metal ions (including heavy metal ions, e.g., ions of lead, cadmium, etc.). The carbon component of the silver-amended carbon material may, in some applications, function as a sorbent and/or ion exchange material. The fluid may be contacted with the silver-amended carbon material for a time and at a temperature effective to purify and/or disinfect the fluid to the desired or target degree. Such contacting may be conducted in a static or dynamic manner. For example, the fluid may be passed through or over a bed comprised of the silver-amended material, either once or repeatedly. The fluid and silver-amended material alternatively could simply be mixed together for a period of time, then separated. Thus, following the contacting of the fluid and the silver-amended carbon material, the fluid phase could be separated from the solid silver-amended carbon material phase to provide recovered silver-amended carbon material and a fluid stream having a reduced microbial level as compared to the initial fluid. The silver and carbon components of the silver-amended carbon materials may work together synergistically, thereby effectively removing or reducing the levels of both microbes and chemical contaminants in a fluid. The potential multiple functionality of the inventive silver-amended carbon materials thus may eliminate the need to incorporate more than one treatment step when purifying fluids containing both microbes and one or more non-microbial contaminants.

Fluids suitable for treatment in accordance with the present invention include, for example, water intended for drinking, cooking and irrigation purposes; air intended for breathing (such as in respirators, HVAC systems, humidifiers/dehumidifiers, oxygen supply devices); fluids used for medical purposes; and the like. Thus, the present invention finds utility in water purification systems for potable, irrigation, or industrial (re)use and air filtration and humidity control systems for individuals, homes, schools, production facilities, buildings, transportation, and other confined personal and public spaces. For example, the silver-amended carbon materials described herein may be employed in centralized and/or point-of-use/point-of-entry (POU/POE) filtration systems and air filtration and humidification systems. Water disinfection and vapor and odor control are other areas in which the present invention can be used. The inventive silver-amended carbon materials can be used to treat drinking water, irrigation water, industrial water, recycled water, humidified air, and other fluids. The silver-amended carbon materials can also be used in food processing and as components of medical devices such as wound dressings and filter cartridges. The microbes which are reduced or eliminated using the silver-amended carbon materials of the present invention may be pathogenic or nonpathogenic and may include bacteria, viruses, protozoa, mold, fungi and the like. The silver-amended carbon materials may be incorporated together with other materials and/or components to form articles useful in any of the above-mentioned applications, such as filter cartridges, filter bags or pouches, membranes, and the like. For example, such articles and applications include athletic attire, sports equipment/accessories, and laundry and bathroom applications.

In certain applications, the silver content of the silver-amended carbon material may be depleted upon prolonged or repeated use. The depleted silver-amended carbon material may be recovered and re-treated with a reducing agent (i.e., restored with electrons) followed by contacting once again with an aqueous solution of silver salt in accordance with the invention to regenerate an active silver-amended carbon material.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the invention. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

The experiment was conducted under an oxygen-free atmosphere. (1) A wood-based biochar (BC) (1 g) was pre-reduced with 25 mM dithionite in 100 mM citrate buffer at pH 6.4 for 3 d. Freshly prepared dithionite solution was added in excess and replenished as needed to ensure complete reduction of the BC. The reduced BC was collected on a glass fiber filter, rinsed thoroughly with deoxygenated deionized water to remove any residual chemicals, and vacuum-dried before exposure to Ag. (2) A known mass (~1 g) of the reduced BC was suspended in 200 L of 100 mM $NaNO_3$ solution in a 1-L amber bottle on an orbital shaker at 100 rpm. After equilibration for 30 min with $NaNO_3$ solution, an aliquot of 100 mM $AgNO_3$ was added to initiate Ag addition to the reduced BC. The aqueous $Ag^+$ concentration was monitored continuously using an $Ag^+$ ion selective electrode (ISE) and an ISE meter. As uptake of $Ag^+$ proceeded and its concentration dropped to <1 mM, another aliquot of $AgNO_3$ was added to maintain the $Ag^+$ concentration. The pH of the solution pH was maintained at a predetermined value (±0.4 pH unit) throughout each experiment using a pH controller. Maximum silver loadings at different pH were obtained from the silver mass balance.

Example 2—Synthesis and Characterization of Silver-Amended Biochar (Ag/BC)

A wood-based biochar having a particle size in the range of 250-500 μm was air-oxidized in continuously aerated deionized water, filtered, and reduced using excess sodium dithionite at a controlled pH under an oxygen-free atmosphere. Based on the electron storage capacity (ESC) of the biochar, which had been measured to be ca. 3.5 mmol/g, a pre-determined quantity of $AgNO_3$ in an aqueous solution also containing $NaNO_3$ was applied to the biochar to produce and deposit silver nanoparticles (nAg) within and also on the exterior of the biochar particles. Maximum silver loadings at different pH values were obtained from silver mass balance based on equilibrium Ag(I) concentrations measured with an ion-specific electrode.

Figure 1:
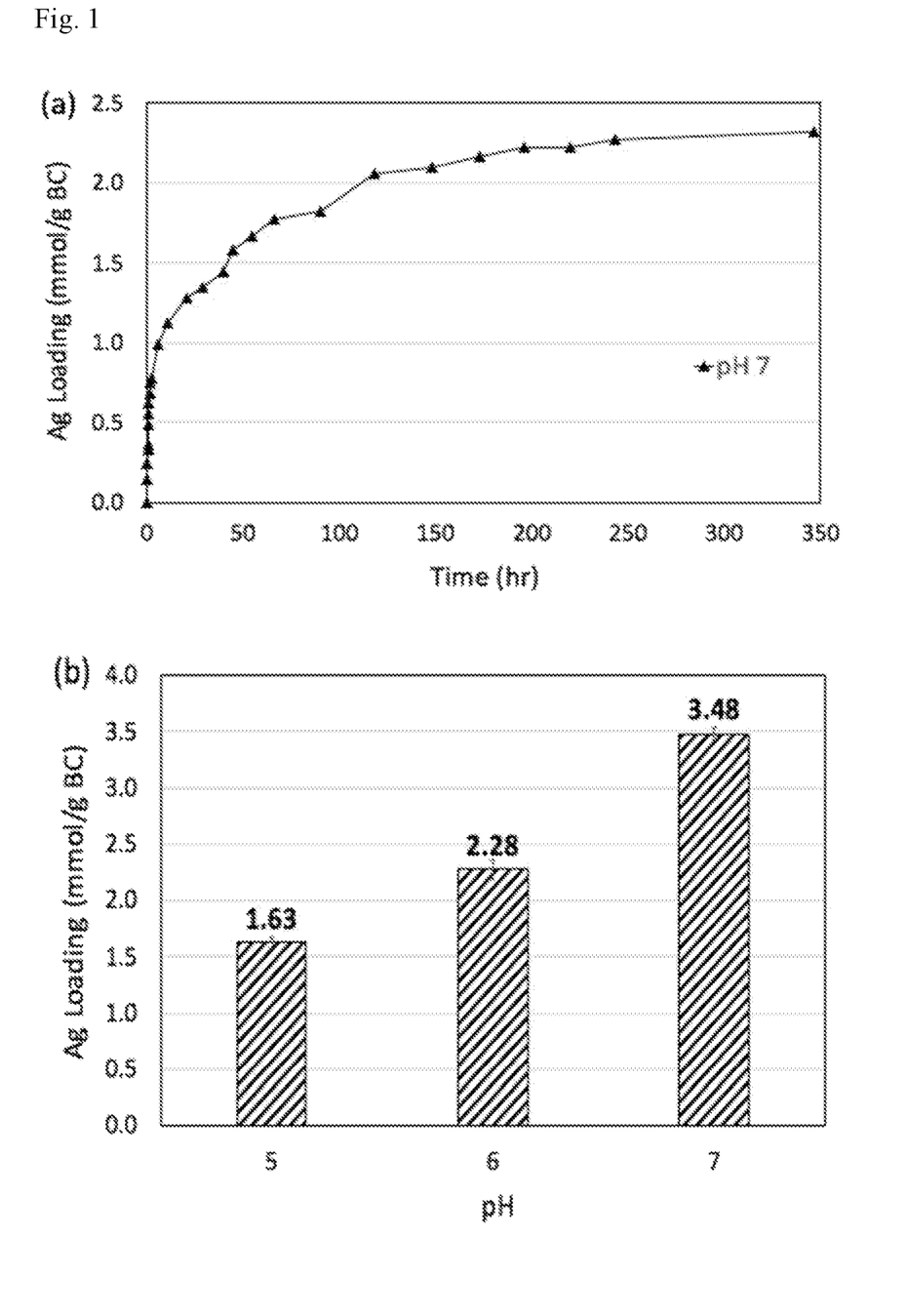
FIGS. 1 and 3-6 illustrate certain experimental results and data, as explained in more detail in the Examples.

The silver loading of the reduced biochar (BC) as a function of time, illustrated with data obtained at pH 7, is shown in FIG. 1($a$). The maximum silver loadings at different solution pH values are shown in FIG. 1($b$).

The process for producing silver-amended carbon materials in accordance with the present invention is flexible and tunable. The process can achieve a desired silver loading by adjusting reaction time, as shown in FIG. 1($a$), by varying solution pH, as shown in FIG. 1($b$), or by controlling both parameters. By adjusting the silver loading, one or both of the antimicrobial potency or the service life of the silver-amended carbon material can be controlled. In this Example, the maximum loading of silver obtained at pH 8 is approaching the ESC of the biochar, indicating that the maximum silver loading achievable can be predicted based on the redox property of the porous carbon material used. At such maximum loading, the silver mass was 37.5% of the biochar (BC) mass, or 27.3% of the total (Ag/BC) mass.

Figure 5:
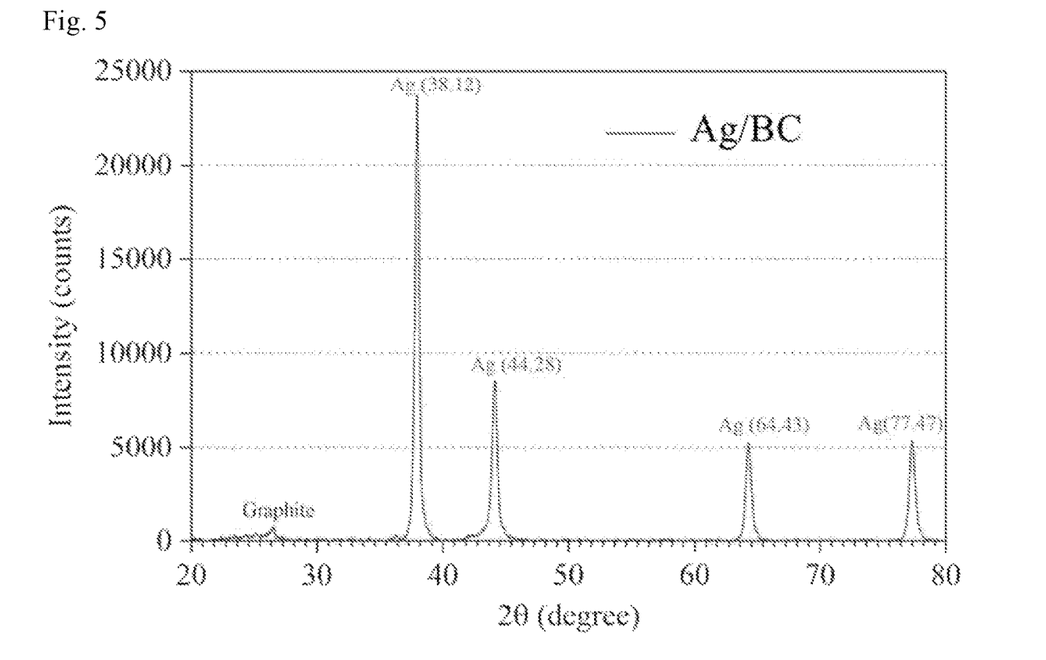

Samples of the original (unmodified) biochar and silver-amended biochar (Ag/BC) were imaged using a scanning electron microscope (SEM Auriga 60) to see the morphology of the BC and Ag/BC and the distribution of silver nanoparticles on the Ag/BC. Samples were also characterized with energy dispersive X-ray spectroscopy (EDX) and X-ray diffraction (XRD), which was conducted using a Bruker D8 XRD (Bruker, MA). The exterior surface of the original biochar (without silver amendment) was relatively smooth and contained few visible nanoparticles. In contrast, the surface of the silver-amended biochar was covered evenly and densely with nanoparticles, most of which were between 25 and 75 nm in size. The average size of the silver nanoparticles on the Ag/BC was determined to be ca. 25 nm by XRD analysis. Using EDX characterization, the nanoparticles on the Ag/BC surface were confirmed to be in the form of Ag(0). Ag nanoparticles were observed not only on the outer (exterior) surface of the Ag/BC, but also over multiple layers of the Ag/BC surface and on the surfaces of inner pores. This was confirmed when the pores were cut by a focused ion beam. The fact that Ag(0) nanoparticles are present in the inner pores of the Ag/BC is consistent with the theory that Ag(0) was formed through reductive deposition of Ag(I) (from the silver nitrate), which entered the biochar interior via slow pore diffusion. The redox state of silver on the Ag/BC was further verified to be Ag(0) by XRD analysis (see FIG. 5). In contrast, no Ag(0) peaks were observed by XRD on the surface of the air-oxidized biochar (BC).

Figure 6:
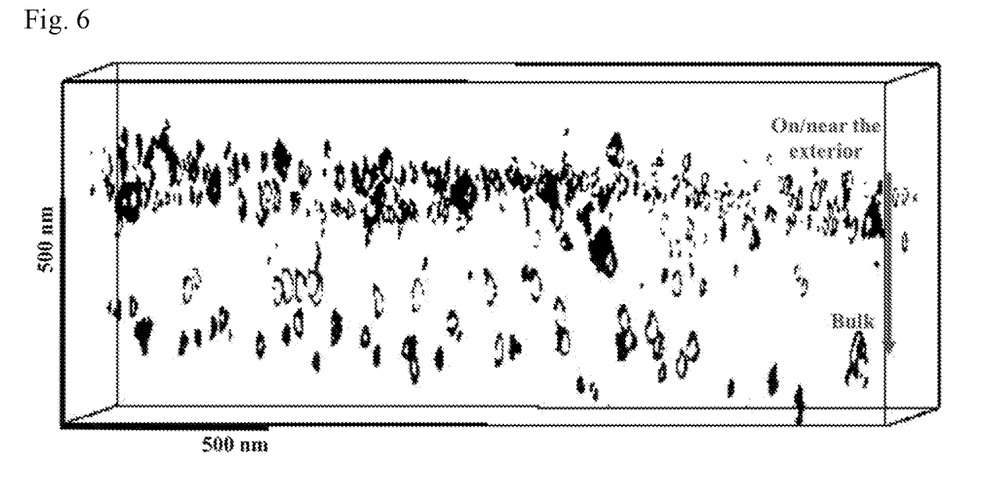

FIG. 6 shows a still image of the scanning transmission electron microscopy (STEM) tomography 3D reconstruction illustrating the spatial distribution of Ag nanoparticles on/within a silver-amended biochar prepared in accordance with the invention (Ag/BC). The STEM images were obtained using a Talos F200C (thermos Fisher Scientific, MA) with a high-angle annular dark-field imaging (HAADF) detector. Tomsgraphy reconstruction was performed with Avizo and Inspect 3D software (Thermo Fisher Scientific, MA).

Example 3—Inactivation of $E.$ $coli$ TVS 353 by Silver-Amended Biochar (Ag/BC)

The effectiveness of an Ag/BC prepared in accordance with Example 2 to inactivate $Escherichia$ $coli$ in simulated irrigation water (10.0 mM $NaHCO_3$ solution, initial pH-adjusted with $NaNO_3$ to 7.1±0.1) was evaluated through batch assays in 125-mL sealable amber glass bottles. $E.$ $coli$ TVS 353 was chosen as a pathogen surrogate and was grown in Tryptic Soy Broth (TSB) to a concentration of about $2.0 \times 10^9$ colony-forming units (CFU)/mL. The total solution volume was 100 mL in all reactors. Assay was initiated by mixing a predetermined mass of Ag/BC suspended in 50mL of 10 mM $NaHCO_3$ solution and 50 mL of diluted $E.$ $coli$ solution which consisted of 49.8 mL of 10 mM $NaHCO_3$ and 0.1 mL of the $E.$ $coli$ stock. Different masses of Ag/BC were tested and the original biochar (no added silver) was used as control. All experiments also included a blank; i.e., 99.9 mL of $NaHCO_3$ and 0.1 mL of $E.$ $coli$ stick, without BC or Ag/Bc.

Figure 2:
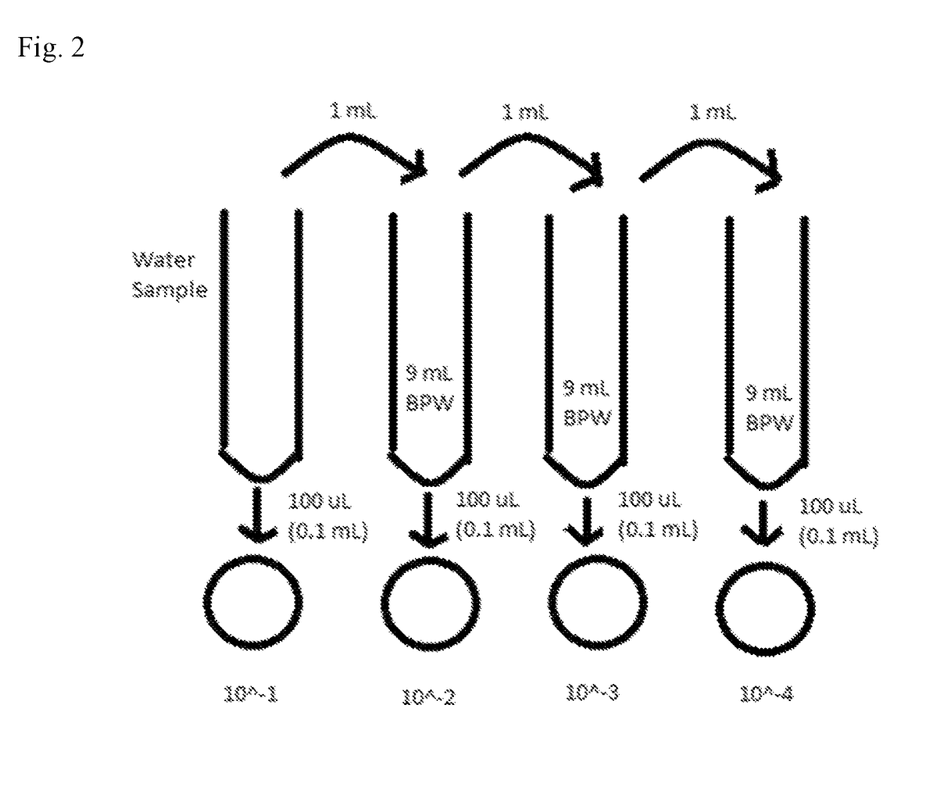
FIG. 2 illustrates in schematic form a serial dilution scheme for quantifying *E. coli* concentration in aqueous samples.

Water samples were taken at time zero and different times after mixing, and $E.$ $coli$ concentration was determined following a standard procedure that involved serial dilutions, plating, incubation, and plate counting, as illustrated in FIG. 2. After dilution, a 0.1-mL sample was collected from each dilution tube and spread on a petri dish, with tryptic soy agar as growth medium. Following plating, the plates were covered and placed in an incubator at 40° C. for 2 days. All time zero samples were in triplicates and all other samples were in duplicates. $E.$ $coli$ colonies were visible on petri dishes and were counted using a colony counter pen. Only plates containing 30-300 colonies were considered countable and were used for quantification.

Figure 3:
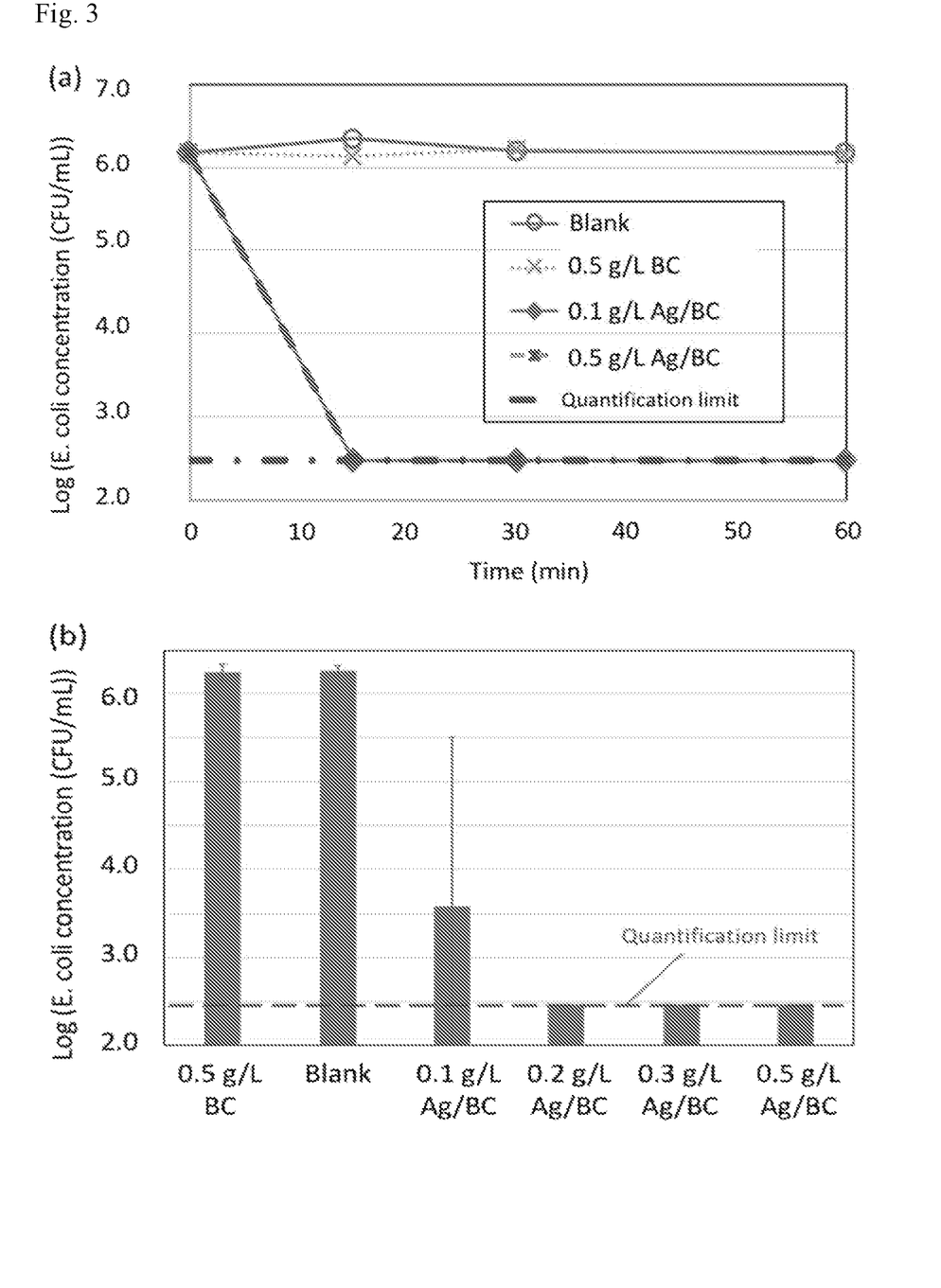

The results of the $E.$ $coli$ inactivation assays are shown in FIG. 3. FIG. 3($a$) shows the inactivation of $E.$ $coli$ TVS 353 after different contact times with the silver-amended biochar. FIG. 3($b$) shows the inactivation of $E.$ $coli$ TVS 353 in water by the silver-amended biochar as a function of the Ag/BC dose. A blank ($E.$ $coli$ only) and unamended biochar (BC) were added as controls. In FIG. 3($a$), BC and Ag/BC were added to $NaHCO_3$ solution two hours before contact. In FIG. 3($b$), the contact time was 15 minutes for all samples. $E.$ $coli$ TVS 353 was stable for over an hour in 10 mM $NaHCO_3$ solution and biochar (BC) without silver addition had no discernable effect on $E.$ $coli$ viability. In the presence of 0.01 g of Ag/BC (in 100 mL solution, or 0.1 g/L), $E.$ $coli$ concentration was below the quantification limit after a contact time of 15 minutes or longer. Similar assays performed at the same dose (0.1 g/L) but a shorter pre-contact exposure time gave lower $E.$ $coli$ inactivation efficiencies (see the large error bar for 0.1 g/L, FIG. 3($b$)). At higher Ag/BC doses, $E.$ $coli$ concentrations were consistently below the quantification limit after 15 min (FIG. 3($b$)).

Example 4—Synthesis and Characterization of Silver-Amended Granular Activated Carbon (Ag/GAC)

This Example demonstrates that the inventive method can also be applied to granular activated carbon, which is the type of black carbon most widely used in water treatment and air purification applications.

A coconut shell-based granular activated carbon (GAC) in the size range of 300-500 μm was reduced using excess sodium dithionite (in aqueous solution) at a controlled pH under an oxygen-free atmosphere. A pre-determined quantity of $AgNO_3$ in an aqueous solution also containing $NaNO_3$ was applied to produce and deposit silver nanoparticles (nAg) onto the reduced GAC. A silver loading of 0.99 mmole per gram of GAC at pH 7 was achieved from silver mass balance based on equilibrium Ag(I) concentrations measured using an Ag(I) selective electrode. At this loading, the silver mass was 10.7% of the GAC mass or 9.7% of the total Ag/GAC mass. The kinetics for Ag loading onto GAS was significantly faster (completed within a few hours) compared to what was observed for biochar (BC), thus highlighting an important advantage of GAC over BC.

Samples of the original (unmodified) GAC and synthesized silver-amended granular activated carbon (Ag/GAC) were imaged using a scanning electron microscope (SEM Auriga 60) to visualize the morphology of the GAC and Ag/GAC and the distribution of silver nanoparticles on the Ag/GAC. Samples of the Ag/GAC were further characterized with energy dispersive X-ray spectroscopy (EDX) and X-ray diffraction (XRD, Bruker).

Nanoscale to microscale pores were found on the exterior surface of the unmodified GAC (without silver amendment), but few nanoparticles were present. After treatment with Ag, the surface of the GAC was covered evenly and densely with Ag nanoparticles, most of which were between 25 and 100 nm. There were also a large number of nanoparticles within the size range of a couple to a few nanometers.

The nanoparticles on the surface of the Ag/GAC were confirmed to be Ag using EDX mapping, with the Ag content being almost 40% on the surface. The species of deposited Ag was further confirmed to be predominantly nano-Ag(0) by XRD analysis.

Elemental Ag(0) crystals were formed on the Ag/GAC, whereas no Ag(0) peaks were observed on the unmodified GAC. This verifies that the redox state of silver on the Ag/GAC was mostly elemental (metallic) Ag(0).

Example 5—Inactivation of *E. coli* TVS 353 by Silver-Amended Granular Activated Carbon (Ag/GAC)

Ag/GAC inactivation experiments using Ag/GAC prepared in accordance with Example 4 were conducted under the same experimental conditions and procedures as described in Example 3, to allow for direct data comparison.

Figure 4:
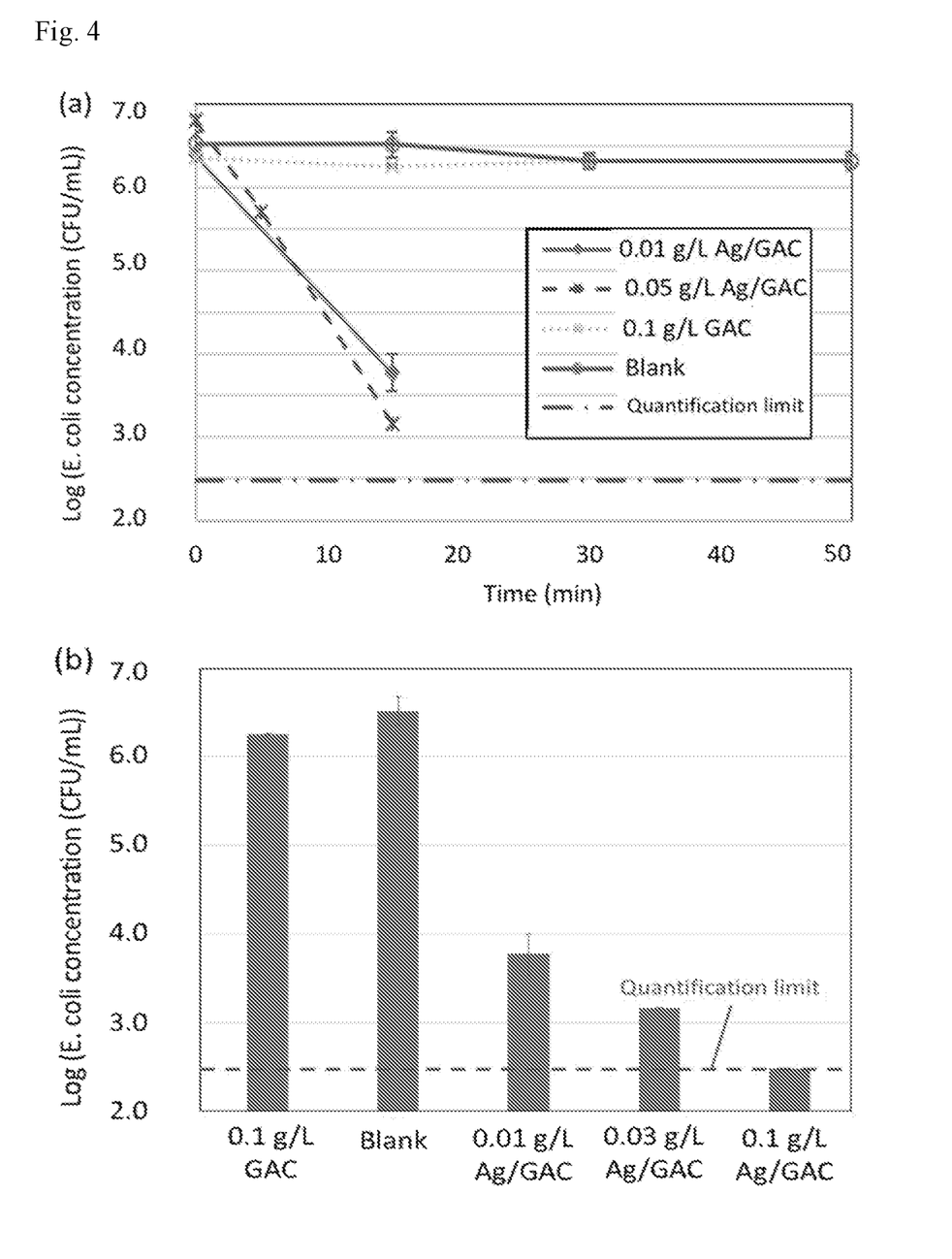

The results of the *E. coli* inactivation assays are shown in FIG. 4. FIG. 4(a) shows the inactivation of *E. coli* TVS 353 after different contact times with the silver-amended granular activated carbon. FIG. 4(b) shows the inactivation of *E. coli* TVS 353 in water by the silver-amended granular activated carbon as a function of the Ag/GAC dose. A blank (*E. coli* only) and unamended granular activated carbon (GAC) were added as controls. In FIG. 4(a), GAC and Ag/GAC were added to $NaHCO_3$ solution two hours before contact. In FIG. 4(b), the contact time was 15 minutes for all samples. *E. coli* TVS 353 was stable for over an hour in 10 mM $NaHCO_3$ solution, and granular activated carbon (GAC, at 1.0 g/L) without added silver had no observable effect on *E. coli* viability. In contrast, in the presence of 0.01 g and 0.03 g of Ag/GAC in 100 mL solution (i.e., 0.1 and 0.3 g/L Ag/GAC, respectively), *E. coli* concentration decreased rapidly and was below the quantification limit after a contact time greater than 15 min. At even higher Ag/GAC doses, *E. coli* concentration dropped even faster, consistently to below the quantification limit in less than 15 minutes (FIG. 4(b)).

What is claimed is:

1. A method of preparing a silver-amended carbon material, comprising a step of:
    contacting a reduced porous carbon material with an aqueous solution containing the silver ion (Ag(I) or $Ag^+$), whereby the reduced porous carbon material acts as a reducing agent with respect to the silver ion and reduces the silver ion to form elemental silver (Ag(0)), which deposits in the form of nanoparticles both on and within the exterior of the reduced porous carbon material,
    wherein the reduced porous carbon material is prepared by contacting a starting porous carbon material having an electron storage capacity with a pre-determined amount of a reducing agent in an aqueous solution to obtain the reduced porous carbon material, wherein the reducing agent is capable of donating electrons to the starting porous carbon material, and
    wherein an amount of silver ion is used which is selected based on the electron storage capacity of the starting porous carbon material.

2. The method of claim 1, wherein the electron storage capacity of the starting porous carbon material is at least 0.5 mmol/g.

3. The method of claim 1, wherein the starting porous carbon material is selected from the group consisting of biochars, activated carbons, pyrolyzed hydrochars, soot, graphite, graphene oxides, fullerenes, char, charcoal, carbon black, and carbon nanotubes.

4. The method of claim 1, wherein the contacting of the reduced porous carbon material with the aqueous solution containing the silver ion is carried out at a pH of from 3 to 8.

5. The method of claim 1, wherein the reducing agent is selected from the group consisting of dithionites, thiosulfates, (poly)sulfides, cysteine, glutathione, titanium (III) compounds and complexes, iron (II) compounds and complexes, borohydrides, aluminum hydrides, hydrazine, and hydroxylamine.

6. The method of claim 1, wherein the aqueous solution containing silver ion comprises a salt selected from the group consisting of silver nitrate, silver sulfate, silver perchlorate, silver acetate, silver nitrite, silver bicarbonate and combinations thereof.

7. The method of claim 1, wherein the contacting of the starting porous carbon material with the pre-determined amount of a reducing agent is carried out under oxygen-free or oxygen-limited conditions.

8. The method of claim 1, wherein the predetermined amount of reducing agent used is an amount which is at least 5% by mole of the electron storage capacity of the starting porous carbon material.

9. The method of claim 1, wherein the predetermined amount of reducing agent is an amount which is in excess by mole of the electron storage capacity of the starting porous carbon material.

10. The method of claim 1, wherein the reduced porous carbon material is fully reduced, as determined by the electron storage capacity.

11. The method of claim 1, wherein the reduced porous carbon material has been collected, optionally rinsed with water and dried, prior to being contacted with the aqueous solution of the silver ion.

12. The method of claim 1, wherein the aqueous solution containing the silver ion is added incrementally to an aqueous suspension of the reduced porous carbon material.

13. The method of claim 12, wherein the aqueous solution containing the silver ion is added at a rate effective to maintain an Ag+ concentration in the aqueous suspension of at least 0.1 mM.

14. The method of claim 1, wherein the silver-amended carbon material is comprised of at least 5% by weight silver based on the total weight of the silver-amended carbon material.

15. The method of claim 1, wherein the silver nanoparticles have an average size of 1 to 100 nm as determined by Scanning Electron Microscopy (SEM) analysis.

16. The method of claim 1, wherein at least 50% of the silver in the silver-amended carbon material is in the form of elemental silver.

17. The method of claim 1, wherein the silver-amended carbon material is in a form selected from the group consisting of powder, granules, fibers, blocks and nanotubes.

18. The method of claim 1, wherein the starting porous carbon material has a BET surface area of at least 10 $m^2/g$.

19. The method of claim 1, wherein the starting porous carbon material has an internal porosity of at least 5%.

20. A silver-amended carbon material produced by the method of claim 1.

21. A method of purifying and disinfecting a fluid containing microorganism(s) comprising contacting the fluid with a silver-amended carbon material produced by the method of claim 1.

22. The method of claim 21, wherein the fluid additionally comprises one or more contaminants selected from the group consisting of organic compounds and metal ions.

* * * * *